US008752979B2

(12) United States Patent
Bauer et al.

(10) Patent No.: US 8,752,979 B2
(45) Date of Patent: Jun. 17, 2014

(54) ILLUMINATION DEVICE FOR A MEDICAL CARE UNIT

(75) Inventors: Georg Bauer, Dachau (DE); Juergen Brunner, Berg (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 402 days.

(21) Appl. No.: 12/236,622

(22) Filed: Sep. 24, 2008

(65) Prior Publication Data

US 2009/0080190 A1    Mar. 26, 2009

(30) Foreign Application Priority Data

Sep. 24, 2007 (DE) .......................... 10 2007 045 456

(51) Int. Cl.
| F21V 1/00 | (2006.01) |
| A61M 21/00 | (2006.01) |
| F21V 14/00 | (2006.01) |
| F21V 33/00 | (2006.01) |
| F21W 131/208 | (2006.01) |
| F21W 131/205 | (2006.01) |

(52) U.S. Cl.
CPC .......... *F21V 14/00* (2013.01); *A61M 2209/084* (2013.01); *A61M 21/00* (2013.01); *A61M 2021/005* (2013.01); *F21W 2131/208* (2013.01); *F21V 33/0068* (2013.01); *F21W 2131/205* (2013.01)
USPC ............. 362/235; 362/11; 362/147; 362/236; 362/238; 362/403

(58) Field of Classification Search
USPC ............ 362/235, 11, 147, 236, 238, 403, 404
See application file for complete search history.

(56) References Cited

U.S. PATENT DOCUMENTS

| 3,769,502 A | 10/1973 | Schultz et al. |
| 4,843,782 A | 7/1989 | Gustaveson et al. |
| 4,849,864 A * | 7/1989 | Forrest .......................... 362/225 |
| 5,038,254 A | 8/1991 | Fabbri et al. |
| 5,160,193 A | 11/1992 | Fabbri et al. |
| 5,526,245 A * | 6/1996 | Davis et al. ................... 362/233 |

(Continued)

FOREIGN PATENT DOCUMENTS

| CA | 1 008 428 | 4/1977 |
| CN | 2886753 | 4/2007 |

(Continued)

OTHER PUBLICATIONS

Extended European Search Report for corresponding European Application No. EP 08 01 6794, mailed Jan. 20, 2009, 5 pages.

(Continued)

Primary Examiner — Jong-Suk (James) Lee
Assistant Examiner — Mark Tsidulko
(74) Attorney, Agent, or Firm — Fish & Richardson P.C.

(57) ABSTRACT

The invention relates to an illumination device for a medical care unit. The illumination device comprises a plurality of light units arranged on a fixing unit to illuminate a room and a display area. At the same time, the color temperature and the distribution thereof as well as the brightness of the individual light units can be tuned to each other, for instance.

17 Claims, 2 Drawing Sheets

(56) References Cited

U.S. PATENT DOCUMENTS

| | | | |
|---|---|---|---|
| 6,328,458 B1* | 12/2001 | Bell et al. | 362/371 |
| 6,443,591 B1 | 9/2002 | Swensson et al. | |
| 6,443,596 B1* | 9/2002 | Bulko et al. | 362/293 |
| 6,639,623 B2* | 10/2003 | Howell et al. | 348/61 |
| 6,644,837 B2* | 11/2003 | Borders et al. | 362/399 |
| 6,683,584 B2* | 1/2004 | Ronzani et al. | 345/8 |
| 6,870,673 B2* | 3/2005 | Cromer et al. | 359/450 |
| 6,880,957 B2* | 4/2005 | Walters | 362/276 |
| 7,097,145 B2* | 8/2006 | Turner | 248/281.11 |
| 7,254,850 B2* | 8/2007 | Newkirk et al. | 5/600 |
| 2001/0030683 A1 | 10/2001 | Howell et al. | |
| 2002/0198438 A1 | 12/2002 | Cromer et al. | |
| 2004/0237202 A1 | 12/2004 | Gallant et al. | |
| 2005/0152144 A1* | 7/2005 | Nash | 362/286 |

FOREIGN PATENT DOCUMENTS

| | | |
|---|---|---|
| DE | 18 48 982 | 3/1962 |
| DE | 3533229 A1 | 3/1987 |
| DE | 3714196 A1 | 11/1988 |
| DE | 4242258 | 4/1994 |
| DE | 29709652 | 11/1998 |
| DE | 20004356 | 6/2000 |
| DE | 201 05 359 | 6/2001 |
| GB | 2 243 223 | 10/1991 |
| JP | 63-14997 | 6/1988 |

OTHER PUBLICATIONS

English translation of office action from corresponding Chinese Application No. 200810165797.5, mailed Apr. 26, 2011, 5 pages.

* cited by examiner

ILLUMINATION DEVICE FOR A MEDICAL CARE UNIT

CROSS REFERENCE TO RELATED APPLICATION

This application claims priority under 35 USC §119(a) from German patent application DE 10 2007 045 456.4, filed Sep. 24, 2007. The complete disclosure of this priority application is incorporated herein by reference.

TECHNICAL FIELD

The invention relates to an illumination device of a medical care unit.

BACKGROUND

Common illumination concepts for illuminating rooms generally include direct room illumination and, where applicable, indirect room illumination which can be arranged, for example, at a wall of the room or within a ceiling bar. The arrangement of the direct and/or indirect room illuminations generally is not adapted to objects which are arranged within the room, such as a sickbed in a sickroom. As a result, patients may be dazzled by the arrangement of the room illumination.

Implementing this type of room illumination generally requires separate electric installation and assembly, which leads to additional work and, therefore, to additional costs, in particular during retrofitting or renovation of the room illumination.

Further, the line of sight of a sleeping patient in the sickroom is mainly directed to the room ceiling. The ceiling may have unsightly air outlets, which is a disadvantage for the patient and does not facilitate the healing progress.

SUMMARY

In one aspect, the invention features an illumination device that includes a fixing unit, a first light unit arranged on the fixing unit, a first light source, arranged within the first light unit, and a translucent display area, arranged on the fixing unit, to which the first light source is directed. The translucent display area is configured to enable illumination of the translucent display area and/or image projection on the translucent display area.

In some implementations, the translucent display area has a shape and dimension such that images can be projected onto the display area, which can improve the patient's comfort during the stay of the patient in the sick-room, since he may watch movies in a horizontal position, for instance. Further, the translucent display area is preferably arranged on a fixing unit so that the patient does not see the room ceiling, which may have unsightly air outlets as well as the parts of the medical care unit arranged above the patient. The sight of the patient is generally directed to the display area which can be evenly illuminated by a first light unit having different brightnesses and different color temperatures, thus providing a more relaxing ambience for the patient. Further, it is generally advantageous that the first light unit and the display area are arranged on the fixing unit, as this tends to reduce the costs for assembling and retrofitting.

In some implementations, a first receiving unit, in which the display area is disposed, can be easily inserted into a second receiving unit and fixed there, e.g., by means of locking elements. Thus, a simple assembly and disassembly of the first receiving unit from the second receiving unit is enabled in order to perform cleaning, disinfection or replacement of the first receiving unit. The second receiving unit can be lowered for ergonomic replacement.

In some implementations the display area is irradiated by light beams which enclose an acute angle, of for example 10°, with the display area. Due to the irradiation of the display area in an acute angle, the display area is evenly illuminated, which in turn provides a relaxing ambience for the patients.

A complete illumination of the room may in some cases be achieved by further light units which include a second, a third and a fourth light source. One of these light sources may be directed to the room floor, another directed to the room ceiling, and another directed to the room sidewalls. Further, the color temperature, the brightness and the distribution of the color temperature, as well as the brightness of the room illumination, can be changed by adjusting these light sources.

Moreover, the color temperatures of the first and the second light units can be tuned to each other, for example so that the whole room, including the display area, is illuminated in the same color temperature. This provides a comfortable ambience for the patients. Further, the light beams of the respective light sources of the second light unit can be directed to the room sidewalls, the room ceiling and the room floor to enclose an acute angle preferably of 10° with the room sidewalls, the room ceiling and the room floor, respectively. Therefore, a more consistent distribution of the room light is enabled.

In some implementations, different positions of the sickbed can be illuminated by a third light unit without dazzling the patient. In some cases, the desired illumination position can be adjusted by the patient himself.

In some cases, the illumination device includes an interface to control the respective light units by a control apparatus. For example, the brightness and spectrum of the light beams can be changed by the control apparatus to stimulate sleep- and waking-cycles. For instance, turning off blue light generally stimulates sleep, since the generation of melatonin is stimulated. Further, the control apparatus can be configured to store fixed illumination cycles, which enables the provision of a pleasant ambience for the patients.

In some implementations, a light sensor is arranged on the illumination device. Incidence of natural light, such as light incidence through a window, is measured by the light sensor. Thereby, the light units can be controlled such that a constant illumination situation is achieved independently from the natural light incidence.

In some cases, a camera is arranged on the illumination device. The camera can be used for communication, or to supplement a personal ward round of the medical scientist by a monitored ward round. Depending on the particular case, the monitored ward round can be continuous, whereby the care situation of the patients is improved and, at the same time, costs can be reduced. The camera can also be used for video telephony in combination with the display area.

The details of one or more embodiments of the invention are set forth in the accompanying drawings and the description below. Other features and advantages of the invention will be apparent from the description and drawings, and from the claims.

DETAILED DESCRIPTION

Figure 1:
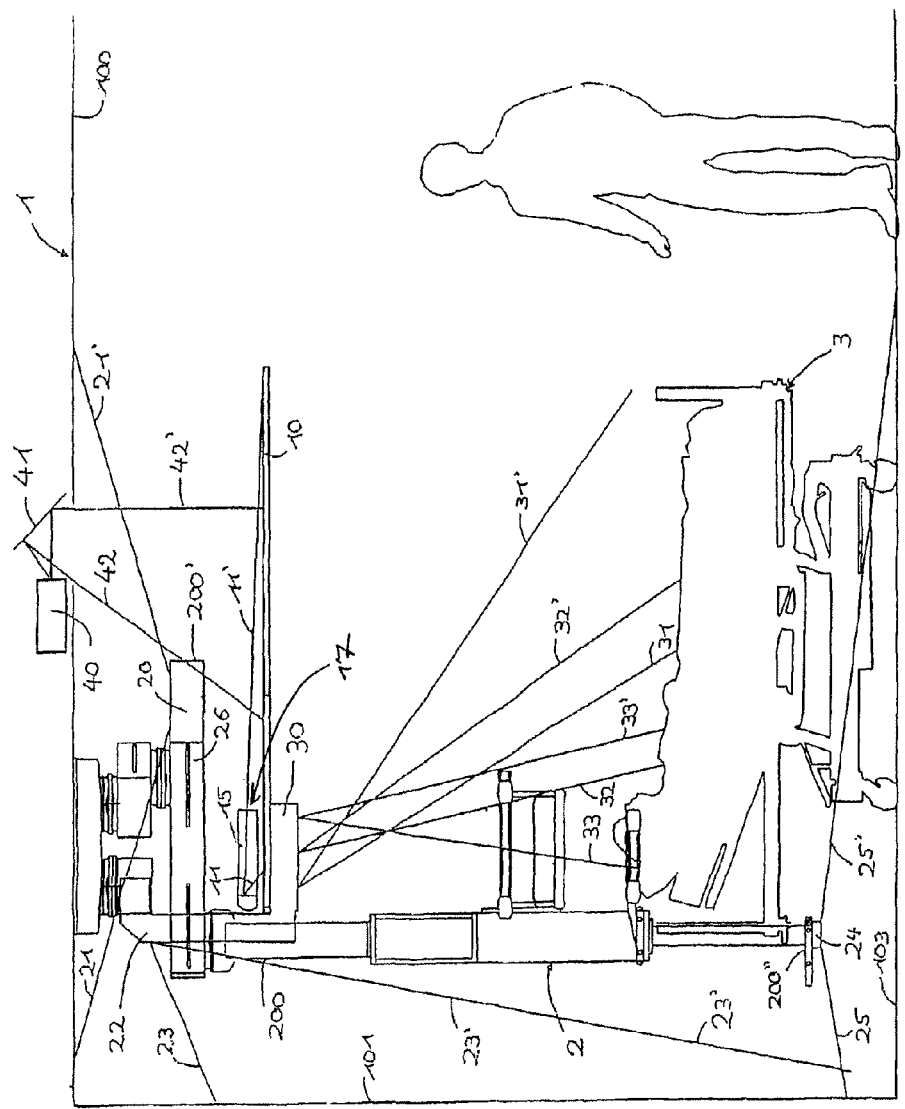
FIG. 1 is a conceptual view of an illumination device with light beams of respective light sources plotted.

Referring to FIG. 1, an illumination device includes a plurality of light sources which are fixed on a medical care unit via illumination units. The medical care unit 2 is disposed within a room 1 and comprises fixing units 200, 200', 200''. Further, a sickbed 3 is arranged within the room 1. A room ceiling 100 comprises a recess through which light beams 42, 42' of an imaging apparatus such as a projector 40 can enter into the room 1. The projector 40 is disposed above the room ceiling 100 parallel thereto. The light beams 42, 42' emitted from the projector 40 are deflected by a mirror 41 so that they enter into the room 1 through the recess. If desired, a plurality of projectors may be used.

The fixing unit 200 is fixed on the medical care unit 2, which in turn is fixed on the ceiling 100, and carries a plurality of light units by which the room 1 is illuminated. Thus, a first light unit 17 is arranged on the fixing unit 200. The first light unit 17 comprises at least one first light source (not shown, as it is within a receiving unit 15 as will be discussed below). The light beams 11, 11' of the first light source illuminate a display area, which is not shown in FIG. 1, of a display unit 10. The first light unit 17 is arranged on the fixing unit 200 in a way that the light beams 11, 11' enclose an acute angle, for example of about 10°, with the display area of the display unit 10. Further, the light beams 42, 42' emitted from the projector 40 are deflected by the mirror 41 so that they reach the display area of the display unit 10, to form the desired image there.

The display unit 10 is arranged parallel to the room ceiling 100 on the fixing unit 200, and has a length and width such that the image formed by the projector 40 can be projected onto the display area arranged on the display unit 10, and the field of vision of the patient is covered as much as possible. Further, the display unit 10 is arranged between the room ceiling 100 and the sickbed 3 so that the image formed by the emitted light beams 42, 42' of the projector 40 is displayed as clearly as possible on the display area. The display unit 10 is configured to hide a part of the room ceiling 100 as much as possible.

Further, a second light unit is arranged on the fixing unit 200, 200', 200'' in order to illuminate the room 1. The second light unit comprises at least one second light source 20 arranged on the fixing unit 200' and directed to the room ceiling 100. At least one third light source 22 is arranged on the fixing unit 200 and directed to the room sidewalls 101, and at least one fourth light source 24 is arranged on the fixing unit 200'' and directed to the room floor. At the same time, the second light source 20 is located on an arm 26 disposed transversely to the fixing unit 200 to thereby illuminate a maximum part of the ceiling 100 by light beams 21, 21' emitted from the second light source.

The third light source 22 is arranged on the end of the fixing unit 200 directed to the room ceiling 100, and it illuminates the room sidewalls 101 by light beams 23, 23'. The fourth light source 24 is arranged on the fixing unit 200'' to illuminate the room floor by light beams 25, 25'. The third and the fourth light sources, 22, 24 can be arranged on the respective fixing units 200, 200'' and/or the second light source 20 can be arranged on the arm 26, and/or they can be configured optically, so that the respective light beams of the second, the third and the fourth light sources 20, 22, 24 enclose an acute angle of preferably 10° with the room ceiling 100, the room sidewalls 101 and the room floors 103, respectively.

Further, the fixing unit 200 comprises a third light unit 30 to illuminate the patient. The light unit 30 comprises at least one fifth light source by which a plurality of sections of the sick-bed 3 can be illuminated independently from each other without dazzling the patient during illumination of the middle and foot sections of the patient. Thereby, three sections of the sickbed can be illuminated in this embodiment. The head section is illuminated by light beams, 33, 33', the middle section is illuminated by light beams 32, 32', and the foot section is illuminated by light beams 31, 31'. The third light unit 30 is shown in detail in FIG. 3 and discussed below.

The control of the individual light units can be performed by the patient himself or by means of an external or integral control apparatus via an interface provided at the fixing units 200, 200', 200''. The first, the second, the third, the fourth and the fifth light sources can be formed as monochrome or color LED's, for example RGB (Tri-Color Red Green Blue) LED's.

Figure 2:
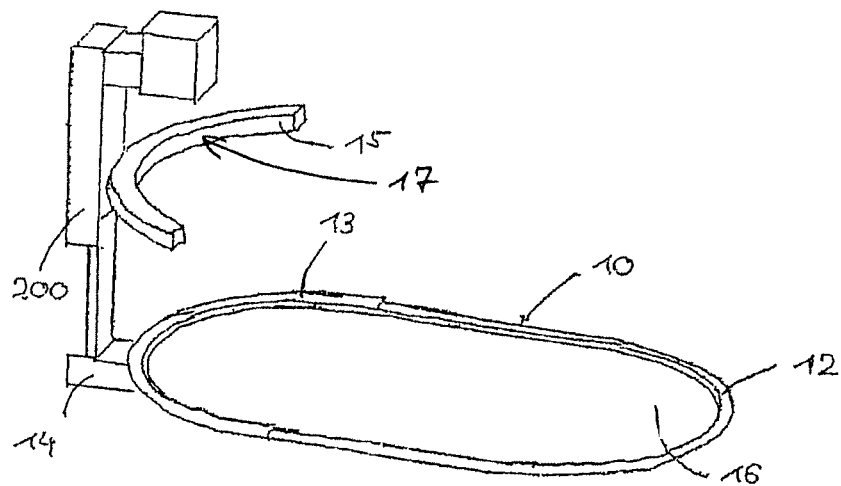
FIG. 2 is a conceptual view of the illumination of a display unit as well as the arrangement thereof on a fixing unit.

FIG. 2 is a concept view of the illumination of the display area and of the arrangement thereof on the fixing unit. The display unit 10 comprises a translucent display area 16 and a first receiving unit 12 in which the display area 16 is arranged. The translucent display area 16 can be formed, for example, of a synthetic material such as polyester, which can be coated, for example with a polyurethane coating. Preferably, the display area 16 has a weak reflection property and a good light dispersion property in order to effect a uniform illumination of the display area 16 during illumination by a light source. At the same time, the display area 16 is also he suitable to bring the light beams into the field of vision of the horizontally lying patient by re-projecting those light beams which are emitted from the projector 40, for instance.

Further, the first receiving unit 12, which is formed as an aluminum tube, for instance, is insertable into a second receiving unit 13. The fixing of the first receiving unit 12 into the second receiving unit 13 can be performed by locking elements, for instance, so that a simple replacement is enabled. Moreover, the second receiving unit 13 is engaged with a holding bracket 14 arranged on the fixing unit 200. The holding bracket 14 can telescopically pulled-out in the vertical direction from the fixing unit 200 to thereby ergonomically disassemble and assemble the display unit 10 in a lower position. Bracket 14 has a vertical thin side and a horizontal thick side. The horizontal side is in conjunction with the second receiving unit 13, while the vertical side is slidably supported in the fixing unit 200. FIG. 1 shows the bracket 14 in an upper, working position, in which the display unit 10 is close to the receiving unit of the first light unit 17. FIG. 2 shows the bracket in a lower position. The distance between the display unit 10 and the first light unit 17 is much greater in this position. In this position, it is easier to assemble/disassemble the display area 10 because a person can reach the display unit 10 with his or her hand.

Further, a U-shaped receiving unit 15 is arranged on the fixing unit 200. Inside this U-shaped receiving unit 15, a first light unit 17 is arranged which comprises at least one first light source. At the same time, the first light source is arranged in the receiving unit and/or provided with optical means such that the light beams 11, 11' emitted from the first light source during illumination of the display area 16 enclose an acute angle of preferably 10° with the display area 16.

Figure 3:
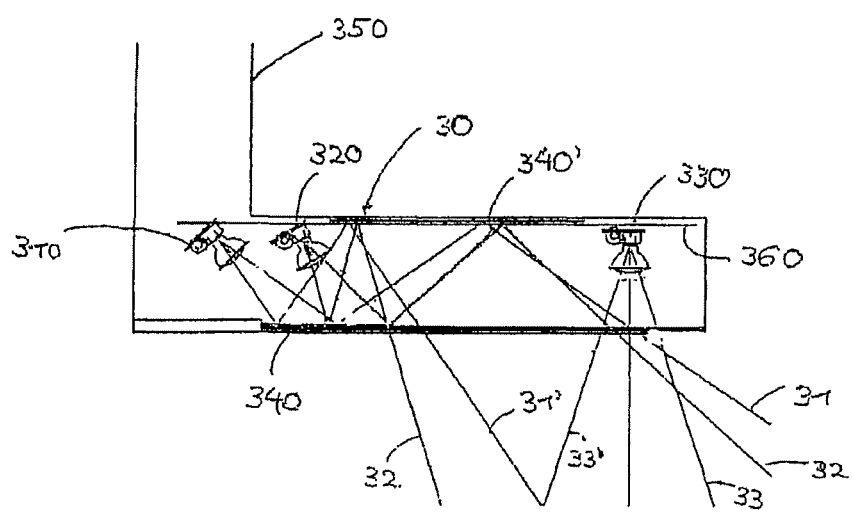
FIG. 3 is a concept view of the illumination of a patient.

FIG. 3 is a more detailed view of the light beams used to illuminate the patient, showing details of a preferred third light unit. In the embodiment shown in FIG. 3, the third light unit 30, shown in FIG. 1 and discussed above, is arranged in a housing 350. In this embodiment, the third light unit 30 comprises three fifth light sources 310, 320, 330. However, more or fewer fifth light sources may be used if desired.

In this embodiment, the fifth light sources 310, 320, 330 are used to illuminate a sickbed, which is not shown in FIG. 3. The fifth light sources 310, 320, 330 can be individually controlled by the patient or by an external or integral control apparatus. Thereby, individual sections of the sickbed can be separately illuminated, for instance. The light beams 31, 31', 32, 32' of the respective fifth light sources 310, 320 are, starting out from the fifth light source, deflected twice by reflection means 340, 340', for example mirrors, which are arranged in the housing 350 so that the patient is not dazzled.

As shown, due to the deflection of the beams by the reflection means, the foot section is illuminated by the first fifth light source 310, the middle section is illuminated by the second fifth light source 320, and the head section of the patient is illuminated by the third fifth light source 330.

Using the illumination device described above, the color temperature and the distribution thereof, as well as the brightness of the individual light units, can be tuned to each other. This can be accomplished by selectively adjusting the color temperature and/or positioning and/or brightness of the individual light units, which are independently adjustable.

A number of embodiments of the invention have been described. Nevertheless, it will be understood that various modifications may be made without departing from the spirit and scope of the invention. Accordingly, other embodiments are within the scope of the following claims.

What is claimed is:

1. An illumination device comprising:
a fixing unit mounted to a room ceiling;
a first light unit arranged on the fixing unit;
a first light source arranged within the first light unit;
a display unit mounted to the fixing unit in a manner such that the display unit is substantially parallel to the room ceiling, the display unit comprising a translucent display area to which the first light source is directed; and
a first receiving unit and a second receiving unit, the second receiving unit being arranged on the fixing unit, the display area being arranged within the first receiving unit, the first receiving unit being insertable into the second receiving unit, and the second receiving unit being slidable perpendicular to the display area,
wherein the first light unit is positioned above the display unit and is configured such that light beams emitted by the first light source illuminate the translucent display area of the display unit, the display unit is configured such that the translucent display area, when illuminated by the light beams emitted by the first light source, is visible to a patient lying on a bed positioned below the display unit and brings the light beams into a field of vision of the patient lying on the bed positioned below the display unit, and the display unit is sized and positioned such that, when the patient is lying on the bed positioned below the display unit, the display unit substantially covers the field of vision of the patient to block the patient's view of the room ceiling.

2. An illumination device according to claim 1, wherein the display area comprises a synthetic fabric.

3. An illumination device according to claim 1, further comprising a third receiving unit, wherein the first light source directed to the display area is arranged in the third receiving unit, the third receiving unit being located above an upper surface of the display area.

4. An illumination device according to claim 3, wherein the third receiving unit is U-shaped.

5. An illumination device according to claim 1, wherein light beams emitted from the first light source directed to the display area enclose an acute angle with the display area.

6. An illumination device according to claim 1, further comprising a second light unit arranged on the fixing unit, the second light unit comprising a second light source configured to be directed to a room ceiling when the device is in use.

7. An illumination device according to claim 6 further comprising a third light source configured to be directed to room sidewalls when the device is in use.

8. An illumination device according to claim 7 further comprising a fourth light source configured to be directed to a room floor when the device is in use.

9. An illumination device according to claim 8, wherein the light sources are configured such that light beams emitted from the second and/or third and/or fourth light sources, enclose an acute angle with the room ceiling, the room sidewalls and the room floor, respectively, when the device is in use.

10. An illumination device according to claim 9, wherein the acute angle has a value of about 10°.

11. An illumination device according to claim 8, further comprising a third light unit fixed on the fixing unit and positioned below a surface of the display area, and a fifth light source arranged in the third light unit.

12. An illumination device according to claim 11, comprising a plurality of fifth light sources, wherein each fifth light source is individually controllable.

13. An illumination device according to claim 1, further comprising a control interface.

14. An illumination device according to claim 1, further comprising a camera.

15. An illumination device according to claim 1, further comprising a light sensor.

16. An illumination device according to claim 1, further comprising a projector positioned above the display unit and configured to project an image downwardly onto the translucent display area of the display unit.

17. An illumination device according to claim 1, wherein the first light unit is a projector configured to project an image downwardly onto the translucent display area of the display unit.

* * * * *